United States Patent [19]

Tobler et al.

[11] Patent Number: 5,036,084
[45] Date of Patent: Jul. 30, 1991

[54] CERTAIN 1-(3-PYRIDYL)-2-PHENOXY-ALKANONES HAVING ANTI-MICROBIAL ACTIVITY

[75] Inventors: Hans Tobler, Allschwil; Peter Ackermann, Pfeffingen; Robert Nyfeler, Basel, all of Switzerland

[73] Assignee: Ciba-Geigy Corporation, Ardsley, N.Y.

[21] Appl. No.: 456,057

[22] Filed: Dec. 21, 1989

Related U.S. Application Data

[63] Continuation of Ser. No. 237,659, Aug. 23, 1988, abandoned, which is a continuation of Ser. No. 912,900, Sep. 26, 1986, abandoned.

Foreign Application Priority Data

Oct. 1, 1985 [CH] Switzerland .......................... 4245/85

[51] Int. Cl.$^5$ .................... C07D 213/46; A01N 43/40
[52] U.S. Cl. ...................................... 514/355; 514/354
[58] Field of Search .................. 546/315; 514/354, 355

[56] References Cited

FOREIGN PATENT DOCUMENTS 0117485  5/1984  European Pat. Off. ............ 546/344
2742173  of 1979  Fed. Rep. of Germany ...... 546/344
223622A5  6/1985  Fed. Rep. of Germany ...... 546/283

OTHER PUBLICATIONS

Grell et al., Chem. Abstracts, vol. 94, (11), Abst. No. 94:83926w, Mar. 16, 1981.

Primary Examiner—Alan L. Rotman
Attorney, Agent, or Firm—George R. Dohmann; Edward McC. Roberts

[57] ABSTRACT

Pyridinyl derivatives of formula I

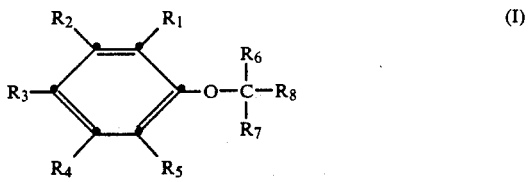

wherein
$R_1$ to $R_5$ are each independently hydrogen, halogen, $C_1$-$C_6$alkyl, $C_1$-$C_6$haloalkyl, $C_1$-$C_6$alkoxy, $C_1$-$C_6$haloalkoxy, cyano, $C_1$-$C_6$alkoxycarbonyl or phenyl,
$R_6$ and $R_7$ are each independently of the other hydrogen, $C_1$-$C_6$alkyl, $C_3$-$C_6$alkenyl or $C_3$-$C_6$alkynyl, or phenyl or benzyl, each of which is unsubstituted or substituted by halogen, $C_1$-$C_6$alkyl, $C_1$-$C_6$haloalkyl, $C_1$-$C_6$alkoxy or $C_1$-$C_6$haloalkoxy,
$R_8$ is

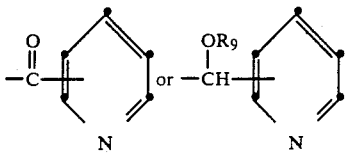

and
$R_9$ is hydrogen, $C_1$-$C_6$alkyl, $C_3$-$C_6$alkenyl, $C_3$-$C_6$alkynyl, or benzyl which is unsubstituted or substituted by halogen, $C_1$-$C_6$alkyl, $C_1$-$C_6$haloalkyl, $C_1$-$C_6$alkoxy or $C_1$-$C_6$haloalkoxy, or $R_9$ is an acyl radical.

The preparation of these compounds and the use thereof in pest control, in particular against bacteria and fungi, are described.

7 Claims, No Drawings

CERTAIN 1-(3-PYRIDYL)-2-PHENOXY-ALKANONES HAVING ANTI-MICROBIAL ACTIVITY

This application is a continuation of Ser. No. 237,659, filed on Aug. 23, 1988, now abandoned, which is a continuation of Ser. No. 912,900, filed on Sept. 26, 1986, now abandoned.

The present invention relates to pyridinyl derivatives, to the preparation thereof and to the use thereof in pest control.

The pyridinyl derivatives have the formula I

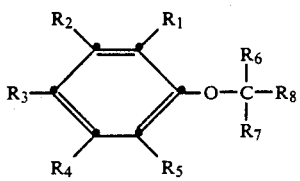

wherein
$R_1$ to $R_5$ are each independently hydrogen, halogen, $C_1$-$C_6$alkyl, 1-$C_6$haloalkoxy, cyano, $C_1$-$C_6$haloalkyl, $C_1$-$C_6$alkoxy, $C_{C1}$-$C_6$alkoxycarbonyl or phenyl, $R_6$ and $R_7$ are each independently of the other hydrogen, $C_1$-$C_6$alkyl, $C_3$-$C_6$alkenyl or $C_3$-$C_6$alkynyl, or phenyl or benzyl, the aromatic ring of each of which may be unsubstituted or substituted by halogen, $C_1$-$C_6$alkyl, $C_1$-$C_6$haloalkyl, $C_1$-$C_6$alkoxy or $C_1$-$C_6$haloalkoxy, $R_8$ is

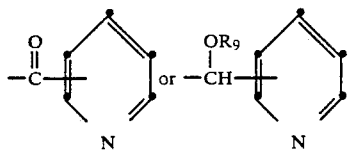

and
$R_9$ is hydrogen, $C_1$-$C_6$alkyl, $C_3$-$C_6$alkenyl, $C_3$-$C_6$alkynyl, or benzyl which may be unsubstituted or substituted at the ring by halogen, $C_1$-$C_6$alkyl, $C_1$-$C_6$haloalkyl, $C_1$-$C_6$alkoxy or $C_1$-$C_6$haloalkoxy, with the proviso that a CO group in the substituent $R_8$ is in the 3- or 4-position of the pyridine ring if $R_1$, $R_2$, $R_4$, $R_5$ and $R_7$ are simultaneously hydrogen, $R_3$ is methoxy and $R_6$ is methyl, and may also be an acyl radical $R_{10}$—CO—, in which $R_{10}$ is $C_1$-$C_6$alkyl, $C_3$-$C_6$alkenyl, $C_3$-$C_6$alkynyl, $C_2$-$C_5$alkoxyalkyl, or $C_1$-$C_6$haloalkyl or is $C_3$-$C_6$cycloalkyl which is unsubstituted or substituted by $C_1$-$C_3$alkyl, or $R_{10}$ is one of the radicals phenyl, benzyl or phenethyl, each of which may be unsubstituted or substituted at the ring by halogen, $C_1$-$C_6$alkyl, $C_1$-$C_6$haloalkyl, $C_1$-$C_6$alkoxy or $C_1C_6$haloalkoxy.

The alkyl, haloalkyl, alkoxy, haloalkoxy, alkenyl and alkynyl radicals $R_1$ to $R_{10}$ may be straight chain or branched.

Depending on the number of indicated carbon atoms, alkyl by itself or as moiety of another substituent such as alkoxy, haloalkyl, haloalkoxy etc. shall be understood as meaning for example the following groups: methyl, ethyl, propyl, butyl, pentyl, hexyl and the isomers thereof, e.g. isopropyl, isobutyl, tert-butyl, isopentyl etc. Halogen and halo stand for fluorine, chlorine, bromine or iodine. Haloalkyl is therefore a mono- to per- halogenated alkyl radical, e.g. $CHCl_2$, $CH_2F$, $CCl_3$, $CH_2Cl$, $CHFCH_3$, $CH_2CH_2Br$, $CF_2CF_3$, $C_2Cl_5$, $CH_2Br$, $CHBrCl$ etc., with $CF_3$ and $CHF_2$ being preferred. Correspondingly, the foregoing examples also apply to haloalkoxy. Alkenyl is e.g. 1-propenyl, allyl, 1-butenyl, 2-butenyl or 3-butenyl as well as chains containing several double bonds. Alkynyl is e.g. 2-propynyl, 1-butynyl, 2-butynyl, 4-pentynyl or, preferably, propargyl. Examples of $C_2$-$C_5$alkoxyalkyl are propoxyethyl, ethoxyethyl, ethoxymethyl, methoxymethyl.

One group of compounds comprises those compounds of formula I wherein $R_1$ to $R_9$ are as defined above, with the exception of the definition $R_{10}$—CO— for the substituent $R_9$.

Preferred compounds of formula I are those wherein $R_1$ to $R_5$ are each independently hydrogen, halogen, $C_1$-$C_4$alkyl, $C_1$-$C_4$haloalkyl, $C_1$-$C_4$alkoxy, $C_{C1}$-$C_4$haloalkoxy, or one of these substituents may also be phenyl, $R_6$ and $R_7$ are each independently of the other hydrogen, $C_1$-$C_6$alkyl, $C_3$-$C_5$alkenyl, $C_3$-$C_5$alkynyl, or phenyl or benzyl, each of which may be substituted at the ring by halogen, and is hydrogen, $C_1$-$C_4$alkyl, $C_3$-$C_4$alkenyl, $C_3$-$C_4$alkynyl, benzyl or halobenzyl, or $R_9$ has the meaning $R_{10}$—CO—, in which $R_{10}$ is $C_1$-$C_4$alkyl, $C_3$-$C_4$alkenyl, $C_3$-$C_4$alkynyl, $C_2$-$C_5$alkoxyalkyl, $C_1$-$C_4$haloalkyl or is $C_3$-$C_6$cycloalkyl which is unsubstituted or substituted by $C_1$-$C_3$alkyl, or $R_{10}$ is one of the radicals phenyl or benzyl, each of which may be unsubstituted or substituted by a maximum of 2 substituents selected from halogen, $C_1$-$C_2$alkyl, $C_1$-$C_2$alkoxy and $C_1$-$C_2$haloalkyl containing 1 to 3 halogen atoms, and $R_8$ is as defined for formula I.

Among these last-named compounds, those compounds of formula I form a group wherein $R_1$ to $R_8$ are as defined above, and $R_9$ is hydrogen, $C_1$-$C_4$alkyl, $C_3$-$C_4$alkenyl, $C_3$-$C_4$alkynyl, benzyl or halobenzyl, and $R_8$ is as defined for formula I (compound group Ia).

One of the important subgroups comprises those pyridinyl derivatives of formula I wherein $R_8$ is CO—(3-pyridinyl) or CH($OR_9$)—(3-pyridinyl) and wherein
$R_1$ is hydrogen, methyl, ethyl or halogen,
$R_2$ is hydrogen,
$R_3$ is hydrogen, halogen, $C_1$-$C_3$haloalkyl, $C_1$-$C_3$haloalkoxy, CN or phenyl,
$R_4$ is hydrogen or halogen,
$R_5$ is hydrogen or halogen,
$R_6$ is $C_1$-$C_4$alkyl, $C_3$-$C_5$alkenyl, $C_3$-$C_5$alkynyl, or phenyl or benzyl, each of which may be substituted at the ring by halogen,
$R_7$ is hydrogen or $C_1$-$C_3$alkyl, and
$R_9$ is hydrogen, $C_1$-$C_4$alkyl, allyl, propargyl, benzyl or $R_{10}$—CO—, in which $R_{10}$ is $C_1$-$C_4$alkyl, $C_3$-$C_4$alkenyl, $C_1$-$C_4$haloalkyl or is $C_3$-$C_6$cycloalkyl which is unsubstituted or substituted by methyl or ethyl.

A further important subgroup comprises those 3-pyridinyl derivatives of formula I wherein the substituents $R_1$ to $R_8$ are as defined above, and wherein $R_6$ is additionally hydrogen, and $R_9$ is hydrogen, $C_1$-$C_4$alkyl, allyl, propargyl or benzyl (compound group Ib).

Within compound group Ib, those compounds are preferred wherein
$R_1$ is hydrogen, fluorine or chlorine,
$R_3$ is fluorine, chlorine or bromine, $CF_3$, $CF_3$—O— or $CHF_2$—O—, $R_2$, $R_4$ and $R_5$ are hydrogen, $R_6$ is hydrogen, $C_2$-$C_4$alkyl, allyl, propargyl, phenyl or chlorophenyl, $R_7$ is hydrogen or methyl, and $R_9$ is hydrogen, methyl, ethyl, isopropyl, allyl or benzyl (compound group Ic). Within compound group Ic, those representatives are particularly preferred wherein $R_6$ is one of the aliphatic substituents mentioned.

Another important subgroup of compounds of formula I comprises those compounds wherein $R_8$ is CO—(3-pyridinyl) or CH(OR$_9$)—(3-pyridinyl), $R_1$ is hydrogen, methyl, fluorine or chlorine, $R_3$ is fluorine, chlorine or bromine, $CF_3$, $CF_3$—O— or $CHF_2$—O—, $R_2$, $R_4$ and $R_5$ are hydrogen, $R_6$ is $C_2$-$C_4$alkyl, allyl, propargyl, phenyl or chlorophenyl, $R_7$ is hydrogen or methyl, and $R_9$ is the group $R_{10}$—CO—, in which $R_{10}$ is $C_1$-$C_4$alkyl, $C_3$-$C_4$alkenyl, $C_1$-$C_2$haloalkyl or $C_3$-$C_5$cycloalkyl which is unsubstituted or substituted by methyl or ethyl.

A preferred subgroup of compounds of formula I comprises those compounds wherein $R_1$ and $R_3$ are chlorine and $R_2$, $R_4$, $R_5$ and $R_7$ are hydrogen, $R_6$ is $C_1$-$C_4$alkyl, and $R_8$ is CO—(3-pyridinyl) or CH(OR$_9$)—(3-pyridinyl), in which $R_9$ is hydrogen or $R_{10}$—CO— and $R_{10}$ is $C_1$-$C_4$alkyl, $C_2$-$C_5$alkoxyalkyl, $C_3$-$C_4$alkenyl, $CF_3$, cyclopropyl or methylcyclopropyl.

Among these last-named compounds, those are particularly preferred wherein $R_{10}$ is methyl, ethyl, propyl, isopropyl, cyclopropyl, butyl, sec-butyl, isobutyl or tert-butyl, and $R_1$ to $R_8$ are as defined.

Among the preferred examples of compounds of formula I are, inter alia, the following representatives:

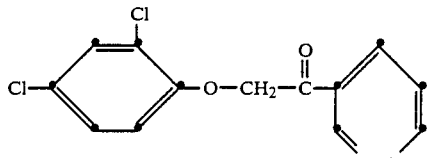

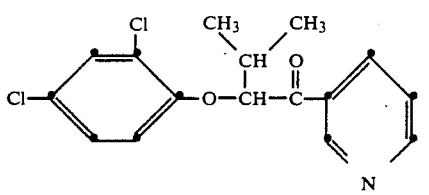

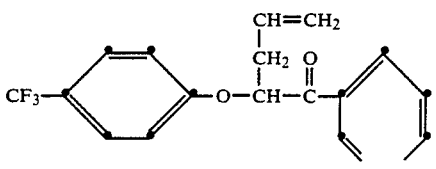

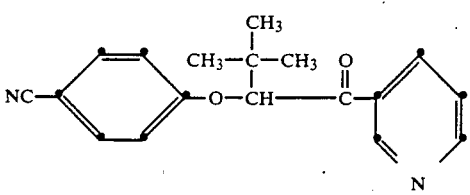

-continued

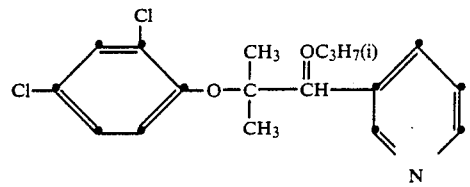

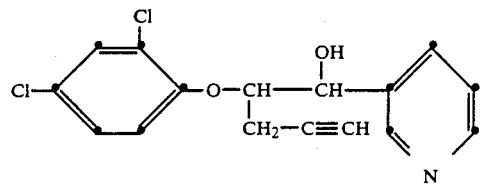

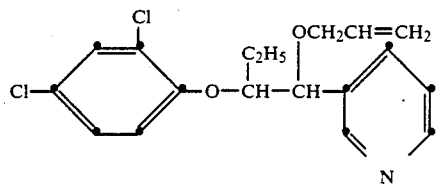

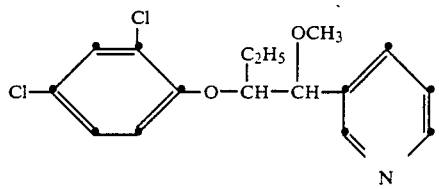

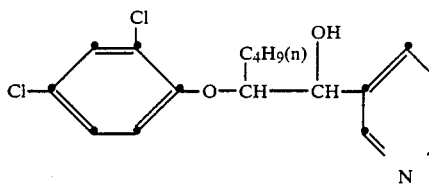

and also the compounds 1-(3-pyridinyl)-2-(2,4-dichlorophenoxy)butan-1-one, 1-(3-pyridinyl)-2-(2,4-dichlorophenoxy)butan-1-ol, 1-(3-pyridinyl)-1-acetoxy-2-(2,4-dichlorophenoxy)butane, 1-(3-pyridinyl)-1-propionyloxy-2-(2,4-dichlorophenoxy)butane, 1-(3-pyridinyl)-1-methoxyacetoxy-2-(2,4-dichlorophenoxy)butane, 1-(3-pyridinyl)-2-(4-chlorophenoxy)hexan-1-one, 1-(3-pyridinyl)-2-(2,4-dichlorophenoxy)pentan-1-ol.

The compounds of formula I wherein $R_8$ is

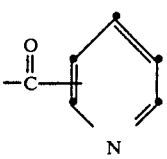

can be prepared e.g. by (a) reacting an ester of formula II

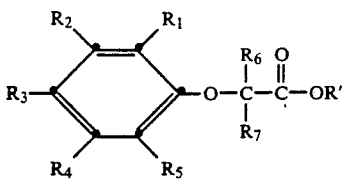 (II)

with a halide of formula III

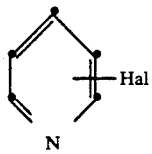 (III)

in the presence of a metallising agent such as Mg (e.g. in the form of a Grignard compound) or butyl lithium or (b) allowing a compound of formula IV

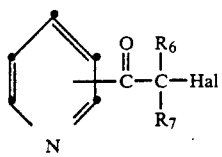 (IV)

to react with a phenol of formula V

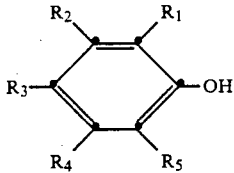 (V)

in the presence of a base, $R_1$ to $R_7$ being as defined for formula I and Hal being halogen, preferably chlorine or bromine, and R' being $C_1$-$C_4$alkyl or $C_3$-$C_4$alkenyl, or phenyl or benzyl, each of which may be unsubstituted or substituted at the ring by alkyl, alkoxy, halogen, $NO_2$ or CN.

Suitable bases for process (b) are in particular tertiary amines such as trialkylamines and pyridine, and also hydroxides, oxides, carbonates and bicarbonates of alkali metals and alkaline earth metals, as well as alkali metal alcoholates, e.g. potassium tert-butylate, or alkali metal hydrides.

To prepare compounds of formula I wherein $R_6$ and/or $R_7$ have a meaning other than hydrogen, it is sometimes advantageous, in a first reaction step, to react a compound of formula IV wherein $R_6=R_7=$hydrogen with the desired phenol of formula V and then, in a subsequent step, to introduce the desired substituent $R_6$ and/or $R_7$ in the form of a compound $R_6$-hal (VIa)

or $R_7$-hal (VIb)

into the resultant compound of formula I at the activated $CH_2$ group, hal in formulae VIa and VIb being halogen, preferably bromine or iodine. This substitution is carried out in the presence of strong bases such as sodium methylate or, preferably, potassium tert-butylate.

Process (a) is carried out either in the absence or, preferably, in the presence of a solvent or diluent and at a temperature in the range from $-130°$ to $+50°$ C., preferably from $-130°$ C. to $+20°$ C.

Process (b) is also preferably carried out in a solvent in the temperature range from $-50°$ to $+150°$ C., preferably from $0°$ to $+120°$ C. Suitable solvents or diluents are inert representatives which do not contain hydroxyl groups, e.g. ethers and ethereal compounds such as diethyl ether, diisopropyl ether, dioxane, 1,2-dimethoxyethane and tetrahydrofuran; amides such as N,N-dialkylated carboxamides of the type dimethylformamide; aliphatic, aromatic and halogenated hydrocarbons, in particular benzene, toluene, xylenes, chloroform and chlorobenzene; nitriles such as acetonitrile; dimethyl sulfoxide and ketones such as acetone or methyl ethyl ketone.

The ketones of formula I prepared by the above processes can be converted by known methods of hydrogenation and, if desired, by subsequent reaction with a compound of formula VII R"Hal (VII)

into compounds of formula I wherein
$R_8$ is

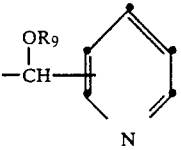

and $R_9$ is hydrogen, $C_1$-$C_6$alkyl, $C_3$-$C_6$alkenyl, $C_3$-$C_6$alkynyl, or benzyl which may be substituted at the ring by halogen, $C_1$-$C_6$alkyl, $C_1$-$C_6$haloalkyl, $C_1$-$C_6$alkoxy or $C_1$-$C_6$haloalkoxy.

R" in formula VII is $C_1$-$C_6$alkyl, $C_3$-$C_6$alkenyl or $C_3$-$C_6$alkynyl, or benzyl which is unsubstituted or substituted at the nucleus by halogen, $C_1$-$C_6$alkyl, $C_1$-$C_6$haloalkyl, $C_1$-$C_6$alkoxy or $C_1$-$C_6$haloalkoxy.

In order to obtain acyl compounds, compounds of formula I wherein $R_9$ is hydrogen can be reacted with a corresponding carboxylic acid $R_{10}$—COOH or with an acid halide (preferably acid chloride or bromide) or acid anhydride thereof. The temperature should be in the range from $-20°$ C. to $+80°$ C. and OH-free solvents or diluents may be used (see above).

Compounds of formulae II to VII are known or they can be prepared by known processes.

If they contain an asymmetric carbon atom, compounds of formula I may be obtained in two enantiomeric forms. In general, when preparing these substances a mixture of both enantiomers forms, which mixture can be resolved in known manner into the pure optical antipodes. Compounds of formula I with two centres of assymetry are also obtained as mixtures of diastereoisomers, which mixtures can be resolved by physical methods. The present invention relates to all pure enantiomers and diastereoisomers and mixtures thereof with one another.

The compounds of formula I of this invention have, for practical application purposes, a very advantageous microbicidal spectrum against phytopathogenic fungi and bacteria. Compounds of formula I have very advantageous curative, systemic and, in particular, preventive properties, and can be used for protecting numerous cultivated plants. With the compounds of formula I it is possible to inhibit or destroy the microorganisms which occur in plants or in parts of plants (fruit, blossoms, leaves, stems, tubers, roots) in different crops of useful plants, while at the same time the parts of plants which grow later are also protected from attack by such microorganisms.

The compounds of formula I are effective against the phytopathogenic fungi belonging to the following classes: Fungi imperfecti (e.g. Botrytis, Helminthosporium, Fusarium, Septoria, Cercospora and Alternaria); Basidiomycetes (e.g. the genera Hemileia, Rhizocotonia, Puccinia); and, in particular, against the class of the Ascomycetes (e.g. Venturia, Podosphaera, Erysiphe, Monilinia, Uncinula). In addition, the compounds of formula I have a systemic action. They can also be used as dressing agents for protecting seeds (fruit, tubers, grains) and plant cuttings against fungus infections as well as against phytopathogenic fungi which occur in the soil. Some of the compounds of formula I also exhibit plant regulating activity and can be used at higher rates of application for curbing excessive vegetative growth in crops of cultivated plants.

The invention also relates to microbicidal compositions as well as to the use of the compounds of formula I for controlling phytopathogenic microorganisms, in particular phytopathogenic fungi, or for protecting plants from attack by said microorganisms.

The invention further embraces the preparation of agrochemical compositions, which comprises homogeneously mixing the active ingredient with one or more compounds or groups of compounds described herein. The invention furthermore relates to a method of treating plants, which comprises applying thereto the compounds of formula I or the novel compositions.

Target crops to be protected within the scope of the present invention comprise e.g. the following species of plants: cereals (wheat, barley, rye, oats, rice, sorghum and related crops), beet (sugar beet and fodder beet), pomes, drupes and soft fruit (apples, pears, plums, peaches, almonds, cherries, strawberries, raspberries and blackberries), leguminous plants (beans, lentils, peas, soybeans), oil plants (rape, mustard, poppy, olives, sunflowers, coconut, castor oil plants, cocoa beans, groundnuts), cucumber plants (cucumber, marrows, melons), fibre plants (cotton, flax, hemp, jute), citrus fruit (oranges, lemons, grapefruit, mandarins), vegetables (spinach, lettuce, asparagus, cabbages, carrots, onions, tomatoes, potatoes, paprika), lauraceae (avocados, cinnamon, camphor), or plants such as maize, tobacco, nuts, coffee, sugar cane, tea, vines, hops, bananas and natural rubber plants, as well as ornamentals (composites).

The structurally closest compound known from the art is 2-(4-methoxyphenoxy)-1-(2-pyridinyl)-1-propanone which is disclosed in German Offenlegungsschrift No. 29 09 754 as an intermediate for the preparation of pharmaceutically active benzofuran derivatives. This compound is not known to have microbicidal activity.

The compounds of formula I are normally applied in the form of compositions and can be applied to the crop area or plant to be treated, simultaneously or in succession, with further compounds. These compounds can be both fertilisers or micronutrient donors or other preparations that influence plant growth. They can also be selective herbicides, insecticides, fungicides, bactericides, nematicides, mollusicides or mixtures of several of these preparations, if desired together with further carriers, surfactants or application promoting adjuvants customarily employed in the art of formulation.

Suitable carriers and adjuvants can be solid or liquid and correspond to the substances ordinarily employed in formulation technology, e.g. natural or regenerated mineral substances, solvents, dispersants, wetting agents, tackifiers, thickeners, binders or fertilisers.

The compounds of formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering, coating or pouring, are chosen in accordance with the intended objectives and the prevailing circumstances. Advantageous rates of application are normally from 50 g to 5 kg of active ingredient (a.i.) per hectare, preferably from 100 g to 2 kg a.i./ha, most preferably from 150 g to 600 g a.i./ha.

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethylene glycol monomethyl ether, ketones such as cyclohexanone, strongly polar solvents such as N-methyl-2-pyrrolidone, dimethyl sulfoxide or dimethylformamide, as well as vegetable oils or epoxidised vegetable oils or soybean oil; or water.

Solid carriers which can be used e.g. for dusts and dispersible powders are calcite, talcum, kaolin, montmorillonite or attapulgite, highly dispersed silicic acid or absorbent polymers. Suitable granulated adsorptive carriers are pumice, broken brick, sepiolite or bentonite; and suitable nonsorbent carriers are e.g. calcite or dolomite. Pregranulated materials may also be used.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

The surfactants customarily employed in the art of formulation are described e.g. in:

"McCutcheon's Detergents and Emulsifiers Annual", MC Publishing Corp., Ridgewood, N.J., 1980;

Sisley and Wood, "Encylopedia of Surface Active Agents", Chemical Publishing Co., Inc., New York, 1980.

Particularly advantageous application promoting adjuvants are also natural or synthetic phospholipids of the series of the cephalins and lecithins, e.g. phospatidyl ethanolamine, phosphatidyl serine, phosphatidyl glycerol and lysolecithin.

The agrochemical compositions usually contain 0.1 to 99%, preferably 0.1 to 95%, of a compound of formula I, 99.9 to 1%, preferably 99.9 to 5%, of a solid or liquid adjuvant, and 0 to 25%, preferably 0.1 to 25%, of a surfactant.

Whereas commercial products will preferably be formulated as concentrates, the end user will normally employ dilute formulations.

The compositions may also contain further auxiliaries such as stabilisers, antifoams, viscosity regulators, binders, tackifiers as well as fertilisers or other active ingredients for obtaining special effects.

EXAMPLE 1: PREPARATORY EXAMPLES FOR COMPOUNDS OF FORMULA I

EXAMPLE 1.1: PREPARATION OF 2-(2,4-DICHLOROPHENOXY)-1-(3-PYRIDINYL)-1-ETHANONE 140.2 g of 93% 2,4-dichlorophenyl and 232 g of potassium carbonate are added to 1000 ml of acetone. After brief heating to boiling temperature, the reaction mixture is cooled to 0° C., and a total of 224.8 g of 3-(bromoacetyl)pyridine hydrobromide are added in portions over one hour. The reaction mixture is stirred for 15 hours at 0° C. to 5° C. and then for 6 hours at 20° C. After filtration and concentration by evaporation of the reaction mixture, the crude product is recrystallised from methanol.

Compound 1 of the formula

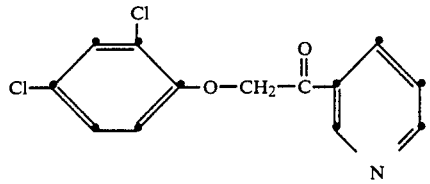

with a melting point of 118°–119° C. is obtained.

EXAMPLE 1.2: PREPARATION OF 2-(2,4-DICHLOROPHENOXY)-1-(3-PYRIDINYL)-1-PROPANONE

With cooling, 17.38 g of 2,4-dichlorophenoxyacetyl-3-pyridine are added to 8.05 g of potassium tert-butylate in 140 ml of dry tetrahydrofuran, the temperature of the solution rising to 35° C. 19.7 g of methyl iodide are added dropwise at 20° C. to the solution. After stirring for 1 hour at 45° C., the crude product is isolated by filtration and then purified by column chromatography (silica gel; eluant a 1:1.5 mixture of ethyl acetate and hexane).

Compound 2 of the formula

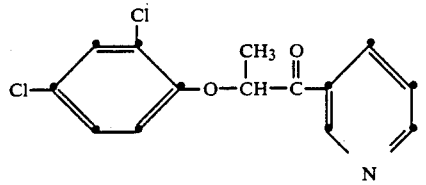

with a refractive index $n_D^{32°}$ of 1.5884 is obtained.

EXAMPLE 1.3: PREPARATION OF 1-(3-PYRIDINYL)-2-METHYL-2-(4-CHLOROPHENOXY)PROPANONE

Under an atmosphere of argon, 12 ml of butyl lithium in 1.6 ml of hexane are dissolved in 50 ml of ether. 2.6 g of 3-bromopyridine are rapidly added at −70° C. After stirring for 30 minutes at −70° C., 3.8 g of ethyl 2-methyl-2-(4-chlorophenoxy)propionate are added to the suspension. After stirring for 30 minutes at −70° C. and for 1 hour at 20° C., 20 ml of saturated ammonium sulfate solution and 5 ml of saturated soda solution are added to the reaction mixture. The mixture is then dried over $Na_2SO_4$, concentrated by evaporation and chromatographed (silica gel; eluant: a 1:2 mixture of ethyl acetate and hexane).

Compound 3 of the formula

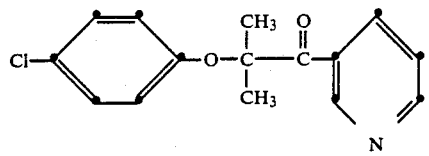

with a melting point of 44°–47° C. is obtained.

EXAMPLE 1.4: PREPARATION OF 1-(3-PYRIDINYL)-2-(2,4-DICHLOROPHENOXY)-BUTAN-1-OL 1.8 g of $NaBH_4$ are added in portions to 11.16 g of 2-(2,4-dichlorophenoxy)butyryl-3-pyridine in 105 ml of methanol. After stirring for 1.5 hours at 40° C., the solution is concentrated by evaporation and taken up in ethyl acetate, and the resultant solution is washed with water and brine, dried and concentrated by evaporation.

The crude product crystallises from a 1:1.5 mixture of ethyl acetate and hexane, affording compound 4 of the formula

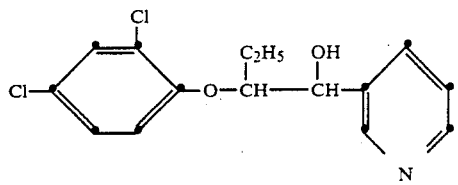

with a melting point of 118°–120° C. (essentially in the form of a pure diastereoisomer).

EXAMPLE 1.5: PREPARATION OF 1-(3-PYRIDINYL)-1-METHOXY-2-(2,4-DICHLOROPHENOXY)BUTANE 4.53 g of 1-(3-pyridyl)-2-(2,4-dichlorophenoxy)butan-1-ol (essentially in the form of a pure diastereoisomer) in 15 ml of tetrahydrofuran are added dropwise to a suspension of 0.8 g of NaH (50% oil dispersion, washed in toluene) in 14 ml of tetrahydrofuran. When the evolution of hydrogen ceases, 10 ml of methyl iodide are added. After 2 hours at 20° C., the ensuing reaction is complete. The reaction mixture is concentrated by evaporation and diluted with water, and the aqueous solution is extracted with ether. The organic phase is separated, washed with water and brine, dried over $Na_2SO_4$, hardened (active carbon) and concentrated by evaporation. The crude product is distilled at 145°–150° C./$10^{-2}$ mbar, affording compound 5 of the formula

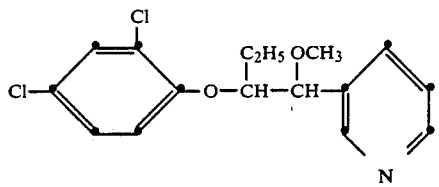

with a refractive index $n_D^{30°}$ of 1.5586 (essentially in the form of a pure diastereoisomer).

EXAMPLE 1.6: PREPARATION OF 1-(3-PYRIDINYL)-2-(2,4-DICHLOROPHENOXY)-1-BUTANONE OF THE FORMULA

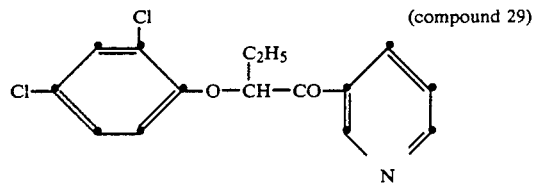
(compound 29)

With slight cooling, 9.2 g of 1-(3-pyridyl)-2-(2,4-dichlorophenoxy)-1-ethanone are slowly added to a solution of 4.15 g of potassium tert-butylate in 45 ml of tetrahydrofuran. 2.9 ml of ethyl iodide are added to the resultant dark red solution. After stirring for 1 hour at room temperature and for 2 hours at 40° C., the solution is concentrated and filtered, and the residue is purified through 450 g of silica gel (eluant: a 1:1.5 mixture of ethyl acetate and hexane), affording 3.4 g of final product with a refractive index $n_D^{30°}$ of 1.5868.

EXAMPLE 1.7: PREPARATION OF 1-ACETOXY-1-(3-PYRIDINYL)-2-(2,4-DICHLOROPHENOXY)BUTANE OF THE FORMULA

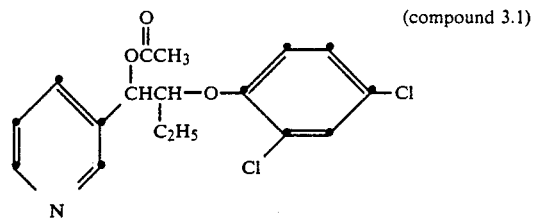
(compound 3.1)

1.8 ml of acetic anhydride are added to 5.2 g of 1-(3-pyridinyl)-2-(2,4-dichlorophenoxy)butan-1-ol (Example 1.4) in 25 ml of pyridine. After stirring at room temperature overnight, the solution is concentrated by evaporation and taken up in ethyl acetate. The resultant solution is washed with water and saturated NaCl solution, dried over $Na_2SO_4$ and concentrated by evaporation, affording 5.0 g of product with a refractive index $n_D^{30°}$ of 1.5521.

Instead of acetic anhydride, it is also possible to employ 1.2 ml of acetyl chloride or acetyl bromide which, dissolved in 5 ml of glacial acetic acid, are added dropwise at about 40° C. to a solution of the same amount of starting material in 25 ml of glacial acetic acid. The reaction mixture is then stirred for 1 hour and worked up.

The following compounds of formula I are also prepared in corresponding manner:

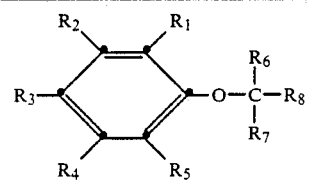

| Comp. | R1 | R2 | R3 | R4 | R5 | R6 | R7 | R8 | Physical data |
|---|---|---|---|---|---|---|---|---|---|
| 6 | H | H | Cl | H | H | H | H | ![pyridinyl-C(=O)-] | m.p.: 107–108° C. |
| 7 | H | H | Br | H | H | H | H | ![pyridinyl-C(=O)-] | m.p.: 118–119° C. |
| 8 | H | H | F | H | H | H | H | ![pyridinyl-C(=O)-] | m.p.: 109–111° C. |

-continued
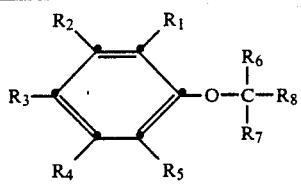
(I)
| Comp. | R₁ | R₂ | R₃ | R₄ | R₅ | R₆ | R₇ | R₈ | Physical data |
|---|---|---|---|---|---|---|---|---|---|
| 9 | H | H | CH$_3$ | H | H | H | H | −C(=O)−(4-pyridyl) | m.p.: 96–97° C. |
| 10 | H | Cl | H | Cl | H | H | H | −C(=O)−(4-pyridyl) | m.p.: 102–104° C. |
| 11 | Cl | H | H | H | H | H | H | −C(=O)−(4-pyridyl) | m.p.: 86–88° C. |
| 12 | H | H | CF$_3$ | H | H | H | H | −C(=O)−(4-pyridyl) | m.p.: 127–129° C. |
| 13 | H | Cl | H | H | H | H | H | −C(=O)−(4-pyridyl) | m.p.: 91–92° C. |
| 14 | H | CF$_3$ | H | H | H | H | H | −C(=O)−(4-pyridyl) | m.p.: 65–67° C. |
| 15 | H | CH$_3$ | Cl | H | H | H | H | −C(=O)−(4-pyridyl) | m.p.: 93–95° C. |
| 16 | H | H | OCH$_3$ | H | H | H | H | −C(=O)−(4-pyridyl) | m.p.: 85–87° C. |

-continued
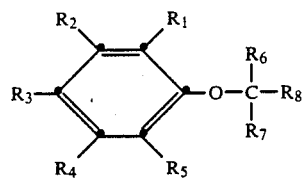
(I)
| Comp. | $R_1$ | $R_2$ | $R_3$ | $R_4$ | $R_5$ | $R_6$ | $R_7$ | $R_8$ | Physical data |
|---|---|---|---|---|---|---|---|---|---|
| 17 | Cl | H | H | H | H | CH$_3$ | H | -C(=O)-(3-pyridyl) | $n_D^{30°} = 1.5821$ |
| 18 | H | Cl | H | H | H | CH$_3$ | H | -C(=O)-(3-pyridyl) | m.p.: 59–61° C. |
| 19 | H | H | Cl | H | H | CH$_3$ | H | -C(=O)-(3-pyridyl) | m.p.: 76–77° C. |
| 20 | H | H | CF$_3$ | H | H | CH$_3$ | H | -C(=O)-(3-pyridyl) | $n_D^{30°} = 1.5220$ |
| 21 | H | CF$_3$ | H | H | H | CH$_3$ | H | -C(=O)-(3-pyridyl) | $n_D^{+°} = 1.5212$ |
| 22 | H | H | F | H | H | CH$_3$ | H | -C(=O)-(3-pyridyl) | m.p.: 71–73° C. |
| 23 | H | H | Br | H | H | CH$_3$ | H | -C(=O)-(3-pyridyl) | m.p.: 69–71° C. |
| 24 | H | H | CH$_3$ | H | H | CH$_3$ | H | -C(=O)-(3-pyridyl) | m.p.: 91–93° C. |

-continued
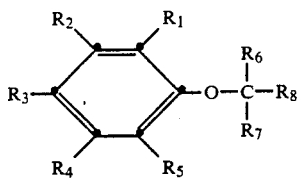
(I)
| Comp. | R₁ | R₂ | R₃ | R₄ | R₅ | R₆ | R₇ | R₈ | Physical data |
|---|---|---|---|---|---|---|---|---|---|
| 25 | H | CH₃ | Cl | H | H | CH₃ | H | -C(=O)-(4-pyridyl) | m.p.: 59–61° C. |
| 26 | H | Cl | H | Cl | H | CH₃ | H | -C(=O)-(4-pyridyl) | $n_D^{30°} = 1.5869$ |
| 27 | Cl | H | Cl | H | H | C₄H₉(t) | H | -C(=O)-(4-pyridyl) | $n_D^{40°} = 1.5601$ |
| 28 | H | H | OCH₃ | H | H | CH₃ | H | -C(=O)-(4-pyridyl) | $n_D^{30°} = 1.5701$ |
| 29 | Cl | H | Cl | H | H | C₂H₅ | H | -C(=O)-(4-pyridyl) | b.p.: 152–154/ 10⁻² mbar |
| 30 | Cl | H | Cl | H | H | C₄H₉(n) | H | -C(=O)-(4-pyridyl) | $n_D^{40°} = 1.5600$ |
| 31 | Cl | H | Cl | H | H | C₃H₇(n) | H | -C(=O)-(4-pyridyl) | $n_D^{30°} = 1.5662$ |
| 32 | H | H | Cl | H | H | C₂H₅ | H | -C(=O)-(4-pyridyl) | $n_D^{30°} = 1.5755$ |

-continued
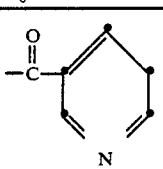
| Comp. | R₁ | R₂ | R₃ | R₄ | R₅ | R₆ | R₇ | R₈ | Physical data |
|---|---|---|---|---|---|---|---|---|---|
| 33 | Cl | H | Cl | H | H | CH₃ | CH₃ | 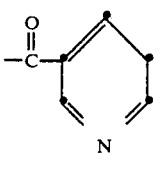 | $n_D^{30°} = 1.5753$ |
| 34 | Cl | H | Cl | H | H | C₂H₅ | CH₃ | 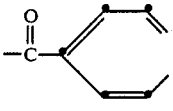 | $n_D^{30°} = 1.5722$ |
| 35 | Cl | H | Cl | H | H | H | H | 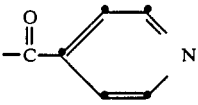 | m.p.: 125–126° C. |
| 36 | Cl | H | Cl | H | H | C₂H₅ | H | 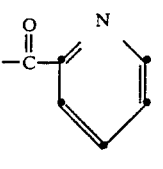 | $n_D^{30°} = 1.5770$ |
| 37 | Cl | H | Cl | H | H | C₂H₅ | H | 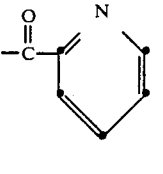 | $n_D^{30°} = 1.5740$ |
| 38 | Cl | H | Cl | H | H | C₃H₇(n) | H | 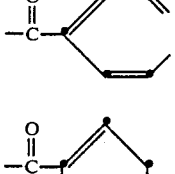 | $n_D^{30°} = 1.5662$ |
| 39 | Cl | H | Cl | H | H | C₃H₇(n) | H | 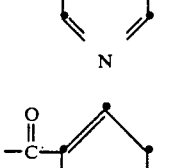 | |
| 40 | Cl | H | Cl | H | H | C₆H₅ | H | 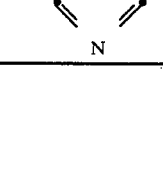 | m.p. 105–107° C. |
| 41 | Cl | H | H | H | H | C₃H₇(i) | H |  | $n_D^{30°} = 1.5705$ |
The following compounds of the formula

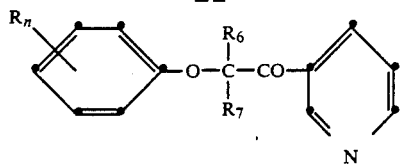

can also be prepared in the same manner or by the methods indicated above (n = index 1, 2 or 3);
Me = methyl, Et = ethyl, nPr = n-propyl, iPr = isopropyl

| Comp. | $R_n$ | $R_6$ | $R_7$ | Physical data |
|---|---|---|---|---|
| 42 | 4-Cl | iPr | H | |
| 43 | 4-Cl | nPr | H | $n_D^{30} = 1.5628$ |
| 44 | 4-Cl | n-butyl | H | $n_D^{40} = 1.5519$ |
| 45 | 4-Cl | Et | Me | |
| 46 | 2-F, 4-Cl | Et | H | |
| 47 | 2-F, 4-Cl | nPr | H | |
| 48 | 2-F, 4-Cl | iPr | H | |
| 49 | 4-F | Et | H | $n_D^{30} = 1.5468$ |
| 50 | 4-F | nPr | H | |
| 51 | 4-F | iPr | H | |
| 52 | 4-Br | Et | H | $n_D^{40} = 1.5809$ |
| 53 | 4-Br | Et | Me | |
| 54 | 4-Br | nPr | H | |
| 55 | 4-Br | iPr | H | |
| 56 | 4-Br | n-butyl | H | |
| 57 | 4-phenyl | Et | H | $n_D^{40} = 1.6083$ |
| 58 | 4-phenyl | nPr | H | |
| 59 | 4-phenyl | iPr | H | |
| 60 | 4-OCH$_3$ | nPr | H | |
| 61 | H | Et | H | |
| 62 | H | nPr | H | |
| 63 | 4-tert-butyl | nPr | H | |
| 64 | 4-methoxy | Et | H | |
| 65 | 4-methoxy | iPr | H | |
| 66 | 4-CF$_3$ | iPr | H | |
| 67 | 3-CF$_3$ | nPr | H | |
| 68 | 4-COOCH$_3$ | Et | H | |
| 69 | 4-CF$_3$O | nPr | H | |
| 70 | 4-CF$_3$O | iPr | H | |
| 71 | 4-CF$_3$O | Et | H | $n_D^{40} = 1.5021$ |
| 72 | 4-CHF$_2$O | Et | H | |
| 73 | 4-CHF$_2$O | nPr | H | |
| 74 | 4-CHF$_2$O | iPr | H | |
| 75 | 4-CN | Et | H | |
| 76 | 2,4-diCl | allyl | H | |
| 77 | 2,4-diCl | propargyl | H | |
| 78 | 3,4-diCl | nPr | H | $n_D^{35} = 1.5713$ |
| 79 | 2,3-diCl | nPr | H | |
| 80 | 3-Cl | Et | H | |
| 81 | 4-CHF$_2$O | Me | Me | |
| 82 | 2,4-diCl | benzyl | H | |
| 83 | 4-Cl | benzyl | H | |
| 84 | 2-Cl, 4-F | Et | H | $n_D^{40} = 1.5514$ |
| 85 | 2-Cl, 4-Br | iPr | H | |
| 86 | 2,4-diF$_2$ | n-butyl | H | |
| 87 | 4-CF$_3$ | Et | H | $n_D^{40} = 1.5125$ |
| 88 | 2,4-diCl | C$_6$H$_4$Cl(4) | H | m.p. 94–96° C. |
| 89 | 4-Cl | C$_6$H$_5$ | H | m.p. 111–113° C. |
| 90 | 4-Cl | C$_6$H$_4$Cl(4) | H | m.p. 86–88° C. |
| 91 | 4-Cl | sec-butyl | H | $n_D^{35} = 1.5559$ |
| 92 | 2,4-diCl | sec-butyl | H | $n_D^{35} = 1.5652$ |
| 93 | 4-Cl | C$_6$H$_4$Cl(2) | H | m.p. 95–97° C. |
| 94 | 2,4-diCl | C$_6$H$_4$Cl(2) | H | highly viscous |
| 95 | 2,4-diCl | C$_6$H$_3$diCl(2,6) | H | highly viscous |
| 96 | 2,4,6-triCl | Et | H | $n_D^{35} = 1.5710$ |
| 97 | 2-CH$_3$,4-Cl | Et | H | $n_D^{35} = 1.5623$ |

The following compounds of the formula

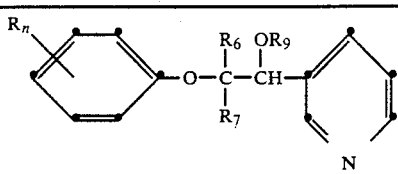

can also be prepared by the procedure of Example 1.4 or 1.5 or by one of the methods indicated above
(n = index, 1, 2, or 3;
Me = methyl, Et = ethyl, nPr = n-Propyl, iPr = isopropyl)

| Comp. | $R_n$ | $R_6$ | $R_7$ | $R_9$ | Physical data |
|---|---|---|---|---|---|
| 2.1 | 4-Cl | Et | H | H | |
| 2.2 | 4-Cl | Et | H | Me | |
| 2.3 | 2,4-diCl | Et | H | allyl | |
| 2.4 | 2,4-diCl | Et | H | propargyl | |
| 2.5 | 2,4-diCl | nPr | H | H | $n_D^{40} = 1.5678$ |
| 2.6 | 2,4-diCl | iPr | H | H | $n_D^{50} = 1.5620$ |
| 2.7 | 2,4-diCl | nPr | H | Me | $n_D^{40} = 1.5491$ |
| 2.8 | 2,4-diCl | iPr | H | Me | $n_D^{30} = 1.5528$ |
| 2.9 | 2,4-diCl | n-butyl | H | H | $n_D^{40} = 1.5531$ |
| 2.10 | 2,4-diCl | n-butyl | H | Me | $n_D^{30} = 1.5470$ |
| 2.11 | 2-Cl, 4-F | Et | H | H | $n_D^{40} = 1.5528$ |
| 2.12 | 2-Cl, 4-F | Et | H | Me | |
| 2.13 | 4-F | nPr | H | Me | |
| 2.14 | 4-Br | n-butyl | H | Me | |
| 2.15 | 2,6-diCl | Me | Me | H | |
| 2.16 | 2,4-diCl | Me | Me | Me | |
| 2.17 | 4-OCH$_3$ | Et | H | H | |
| 2.18 | 4-CF$_3$ | nPr | H | H | |
| 2.19 | 4-CF$_3$ | nPr | H | Me | |
| 2.20 | 4-CF$_3$O | Et | H | H | |
| 2.21 | 4-CF$_3$O | Et | H | Et | |
| 2.22 | 4-CN | Et | H | Me | |
| 2.23 | 2,4-diF | n-butyl | H | Me | |
| 2.24 | 3,4-diCl | Et | H | H | |
| 2.25 | 2,3-diCl | nPr | H | H | |
| 2.26 | 2,3-diCl | nPr | H | Me | |
| 2.27 | 4-Me | Et | H | Me | |
| 2.28 | 2,4-diCl | phenyl | H | H | |
| 2.29 | 2,4-diCl | phenyl | H | Me | |
| 2.30 | 2,4-diCl | Me | H | H | m.p. 88–100° C. |
| 2.31 | 2,4-diCl | Me | H | Me | $n_D^{31} = 1.5642$ |
| 2.32 | 2,4-diCl | H | H | H | m.p. 117–119° C. |
| 2.33 | 2,4-diCl | H | H | Me | $n_D^{31} = 1.5716$ |
| 2.34 | 2,4,6-triCl | Et | H | H | m.p. 118–121° C. |
| 2.35 | 2-CH$_3$,4-Cl | Et | H | H | m.p. 69–72° C. |

The following acyl compounds are also prepared by the procedure of Example 1.7

[structure shown]

| Comp. | $R^{10}$ | $R^6$ | Physical data |
|---|---|---|---|
| 3.1 | —CH$_3$ | C$_2$H$_5$ | $n_D^{30} = 1.5521$ |
| 3.2 | —CH$_2$CH$_3$ | C$_2$H$_5$ | $n_D^{30} = 1.5470$ |
| 3.3 | —CH$_2$CH$_2$CH$_3$ | C$_2$H$_5$ | $n_D^{30} = 1.5398$ |
| 3.4 | CF$_3$ | C$_2$H$_5$ | $n_D^{30} = 1.5188$ |
| 3.5 | —C(CH$_3$)$_3$ | C$_2$H$_5$ | $n_D^{30} = 1.5350$ |
| 3.6 | —C$_6$H$_4$—CH$_3$ | C$_2$H$_5$ | $n_D^{30} = 1.5783$ |
| 3.7 | —C$_6$H$_5$ | C$_2$H$_5$ | $n_D^{30} = 1.5774$ |

-continued

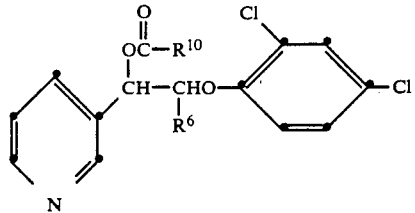

| Comp. | R¹⁰ | R⁶ | Physical data |
|---|---|---|---|
| 3.8 | 4-Cl-phenyl | $C_2H_5$ | $n_D^{30} = 1.5831$ |
| 3.9 | 2-CF₃-phenyl | $C_2H_5$ | $n_D^{30} = 1.5408$ |
| 3.10 | 4-Cl-phenyl | $C_2H_5$ | $n_D^{35} = 1.5824$ |
| 3.11 | 3,4-di-Cl-phenyl | $C_2H_5$ | $n_D^{35} = 1.5882$ |
| 3.12 | 2-OCH₃-phenyl | $C_2H_5$ | $n_D^{30} = 1.5781$ |

-continued

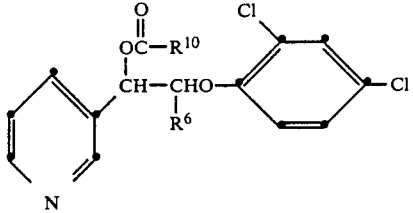

| Comp. | R¹⁰ | R⁶ | Physical data |
|---|---|---|---|
| 3.13 | $CH_3$ | $C_4H_9(n)$ | $n_D^{30} = 1.5395$ |
| 3.14 | $CH_2OCH_3$ | $C_2H_5$ | $n_D^{30} = 1.5471$ |
| 3.15 | $CH_2OCH_3$ | $C_4H_9(n)$ | $n_D^{30} = 1.5400$ |
| 3.16 | phenyl | $C_4H_9(n)$ | $n_D^{30} = 1.5702$ |
| 3.17 | 4-Cl-phenyl | $C_4H_9(n)$ | $n_D^{30} = 1.5739$ |
| 3.18 | 4-CH₃-phenyl | $C_4H_9(n)$ | $n_D^{30} = 1.5673$ |
| 3.19 | 2-CF₃-phenyl | $C_4H_9(n)$ | $n_D^{30} = 1.5396$ | as well as the following acyl compounds

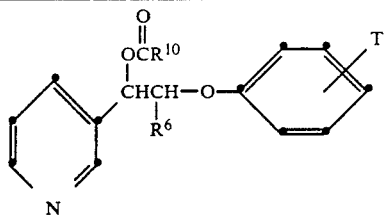

| Comp. | R¹⁰ | R⁶ | T | Physical data |
|---|---|---|---|---|
| 4.1 | —C₃H₇(iso) | $C_2H_5$ | 2,4-di-Cl | $n_D^{30} = 1.5394$ |
| 4.2 | cyclopropyl | $C_2H_5$ | 2,4-di-Cl | $n_D^{30} = 1.5559$ |
| 4.3 | —CH₂CH₂CH₃ | $C_4H_9(n)$ | 2,4-di-Cl |  |
| 4.4 | —CH₂CH₃ | $C_4H_9(n)$ | 2,4-di-Cl | $n_D^{30} = 1.5388$ |
| 4.5 | —CH₃ | $C_2H_5$ | 4-Cl |  |
| 4.6 | —CH₃ | $C_4H_9(n)$ | 4-Cl |  |
| 4.7 | CH₃ | $C_3H_7(n)$ | 2,4-di-Cl |  |
| 4.8 | CH₂CH₃ | $C_3H_7(n)$ | 2,4-di-Cl |  |
| 4.9 | CH₂CH₂CH₃ | $C_3H_7(n)$ | 2,4-di-Cl |  |
| 4.10 | C₃H₇(iso) | $C_3H_7(n)$ | 2,4-di-Cl |  |
| 4.11 | —CH₂CH₃ | $C_3H_7(n)$ | 4-Cl |  |
| 4.12 | —CH₂CH₃ | $C_3H_7(iso)$ | 2,4-di-Cl | $n_D^{50} = 1.5350$ |

-continued

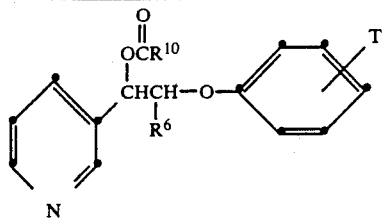

| Comp. | R$^{10}$ | R$^6$ | T | Physical data |
|---|---|---|---|---|
| 4.13 | —CH$_3$ | C$_3$H$_7$(iso) | 2,4-di-Cl | m.p. 116–117° C. |
| 4.14 | —C$_6$H$_4$Cl(4) | C$_3$H$_7$(n) | 2,4-di-Cl | |
| 4.15 | —C$_6$H$_5$ | C$_3$H$_7$(n) | 2,4-di-Cl | |
| 4.16 | —C$_6$H$_3$Cl$_2$(2,4) | C$_3$H$_7$(n) | 2,4-di-Cl | |
| 4.17 | —C(C$_2$H$_5$)=CH$_2$ | C$_2$H$_5$ | 2,4-di-Cl | |
| 4.18 | —C(CH$_3$)$_3$ | C$_3$H$_7$iso | 2,4-di-Cl | $n_D^{50} = 1.5250$ |
| 4.19 | —C$_2$H$_5$ | C$_3$H$_7$iso | 2,4-di-Cl | |
| 4.20 | —C$_3$H$_7$iso | C$_3$H$_7$iso | 2,4-di-Cl | $n_D^{50} = 1.5294$ |
| 4.21 | ▷ | C$_3$H$_7$iso | 2,4-di-Cl | $n_D^{50} = 1.5425$ |
| 4.22 | ▷ | C$_4$H$_9$n | 2,4-di-Cl | $n_D^{30} = 1.5468$ |
| 4.23 | —C$_3$H$_7$iso | C$_4$H$_9$n | 2,4-di-Cl | $n_D^{30} = 1.5312$ |
| 4.24 | —C(CH$_3$)$_3$ | C$_4$H$_9$n | 2,4-di-Cl | $n_D^{30} = 1.5284$ |
| 4.25 | CH$_3$ | C$_2$H$_5$ | 2-CH$_3$, 4-Cl | $n_D^{30} = 1.5484$ |
| 4.26 | CH$_3$ | C$_2$H$_5$ | 2,4,6-tri-Cl | $n_D^{30} = 1.5603$ |
| 4.27 | CH$_3$ | C$_2$H$_5$ | 2-Cl, 4-F | $n_D^{30} = 1.5496$ |
| 4.28 | CF$_3$ | C$_3$H$_7$iso | 2,4-di-Cl | |
| 4.29 | ▷—CH$_3$ | C$_3$H$_7$iso | 2,4-di-Cl | |

EXAMPLE 2: FORMULATION EXAMPLES FOR ACTIVE INGREDIENTS OF FORMULA I ACCORDING TO THE PREPARATORY EXAMPLES OR TABLES 1 TO 4

(throughout, percentages are by weight)

| 2.1. Emulsifiable concentrates | (a) | (b) | (c) | (d) |
|---|---|---|---|---|
| compound according to the Preparatory Examples or Tables 1 to 4 | 10% | 25% | 40% | 50% |
| calcium dodecylbenzenesulfonate | — | 5% | 8% | 6% |
| castor oil polyethylene glycol ether (36 moles of ethylene oxide) | — | 5% | — | — |
| tributylphenol polyethylene glycol ether (30 moles of ethylene oxide) | — | — | 12% | 4% |
| castor oil thioxilate | 25% | — | — | — |
| cyclohexanone | — | — | 15% | 20% |
| butanol | 15% | — | — | — |
| xylene mixture | — | 65% | 25% | 20% |
| ethyl acetate | 50% | — | — | — |

Emulsions of any required concentration can be produced from such concentrates by dilution with water.

| 2.2. Solutions | (a) | (b) |
|---|---|---|
| compound according to the Preparatory Examples or Tables 1 to 4 | 10% | 5% |
| ethylene glycol monomethyl ether | — | — |
| polyethylene glycol (mol. wt. 400) | 70% | — |
| N-methyl-2-pyrrolidone | 20% | — |
| expoxidised coconut oil | — | 1% |
| ligroin (boiling range 160–190° C.) | — | 94% |

These solutions are suitable for application in the form of microdrops.

| 2.3. Wettable powders | (a) | (b) | (c) |
|---|---|---|---|
| compound according to the Preparatory Examples or Tables 1 to 4 | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| 2.4. Suspension concentrate | |
|---|---|
| compound according to the Preparatory Examples or Tables 1 to 4 | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

EXAMPLE 3: BIOLOGICAL EXAMPLES

EXAMPLE 3.1.: ACTION AGAINST *PUCCINIA GRAMINIS* ON WHEAT a) Residual-Protective Action Wheat plants are treated 6 days after sowing with a spray mixture (0.02% active ingredient) prepared from a wettable powder formulation of the test compound. After 24 hours the treated plants are infected with a uredospore suspension of the fungus. The infected plants are incubated for 48 hours at 95-100% relative humidity and about 20° C. and then stood in a greenhouse at about 22° C. Evaluation of rust pustule development is made 12 days after infection.

b) Systemic Action

Wheat plants are treated 5 days after sowing with a spray mixture (0.006% active ingredient, based on the volume of the soil) prepared from a wettable powder formulation of the test compound. After 48 hours the treated plants are infected with a uredospore suspension of the fungus. The plants are then incubated for 48 hours at 95-100% relative humidity and about 20° C. and then stood in a greenhouse at about 22° C. Evaluation of rust pustule development is made 12 days after infection.

Compounds of the Tables exhibit very good activity against Puccinia fungi. Puccinia attack is 100% on untreated and infected control plants. The compounds 2-7, 19, 29, 30, 2.5-2.8, 2.11, 2.34, 3.1, 3.2, 3.14, 4.1, 4.2, 4.4, 4.22-4.27 inhibit Puccinia attack to 10% or less.

EXAMPLE 3.2.: ACTION AGAINST CERCOSPORA ARACHIDICOLA ON GROUNDNUT PLANTS

Residual Protective Action

Groundnut plants 10-15 cm in height are sprayed with a spray mixture (0.006% active ingredient) prepared from a wettable powder formulation of the test compound, and infected 48 hours later with a conidia suspension of the fungus. The infected plants are incubated for 72 hours at about 21° C. and high humidity and then stood in a greenhouse until the typical leaf specks occur. Evaluation of the fungicidal action is made 12 days after infection and is based on the number and size of the specks.

Compared with untreated and infected control plants (number and size of the specks=100%), Cercospora attack on groundnut plants treated with compounds of the Tables is substantially reduced. The compounds 2, 19, 29, 2.5, 2.6, 2.7, 2.8, 2.11, 3.1, 3.2, 4.1, 4.2, 4.4, 4.25 and others inhibit the occurrence of specks almost completely (0 to 10%) in the above test.

EXAMPLE 3.3.: ACTION AGAINST ERYSIPHE GRAMINIS ON BARLEY a) Residual Protective Action Barley plants about 8 cm in height are sprayed with a spray mixture (0.002% active ingredient) prepared from a wettable powder formulation of the test compound. The treated plants are dusted with conidia of the fungus after 3 to 4 hours. The infected barley plants are stood in a greenhouse at about 22° C. The fungus attack is evaluated after 10 days.

b) Systemic Action

A spray mixture (0.0006% active ingredient, based on the volume of the soil) prepared from a wettable powder formulation of the test compound is poured onto barley plants about 8 cm in height. Care is taken that the spray mixture does not come into contact with the parts of the plants above the soil. The treated plants are infected 48 hours later with a conidia suspension of the fungus. The infected barley plants are then stood in a greenhouse at about 22° C. and evaluation of infestation is made after 10 days.

Compounds of formula I exhibit good activity against Erysiphe fungi. Erysiphe attack is 100% on untreated and infected control plants. The compounds 2, 3, 5, 8, 19, 20, 23, 27, 29, 30, 96, 97, 2.5-2.11, 2.30-2.35, 3.1-3.3, 3.11, 3.13-3.15, 3.19, 4.1, 4.2, 4.4, 4.22-4.23 and others inhibit fungus attack on barley to 0 to 5%.

EXAMPLE 3.4.: RESIDUAL-PROTECTIVE ACTION AGAINST *VENTURIA INAEQUALIS* ON APPLE SHOOTS

Apple cuttings with 10-20 cm long fresh shoots are sprayed with a spray mixture (0.006% active ingredient) prepared from a wettable powder formulation of the test compound. The plants are infected 24 hours later with a conidia suspension of the fungus. The plants are then incubated for 5 days at 90-100% relative humidity and stood in a greenhouse for a further 10 days at 20°-24° C. Evaluation of scab infestation is made 15 days after infection. Compounds of formula I inhibit attack to less than 10%, e.g. compounds 29, 30, 3.1, 3.2 and others. Venturia attack on untreated and infected shoots is 100%.

EXAMPLE 3.5.: ACTION AGAINST *BOTRYTIS CINEREA* ON BEANS

Residual Protective Action

Bean plants about 10 cm in height are sprayed with a spray mixture (0.02% active ingredient) prepared from a wettable powder formulation of the test compound. After 48 hours the treated plants are infected with a conidia suspension of the fungus. The infected plants are incubated for 3 days at 95-100% relative humidity and 21° C. and then evaluated for fungus attack. Many of the compounds of the Tables inhibit fungus infection very strongly. At a concentration of 0.02% the compounds of formula I are completely effective. Attack is 10% or less, e.g. after treatment with compounds 3, 5, 11, 29, 30, 2.5-2.8, 3.1, 3.2, 4.1, 4.4, 4.23. Botrytris attack on untreated and infected bean plants is 100%.

EXAMPLE 3.6.: ACTION AGAINST *PYRICULARIA ORYZAE* ON RICE PLANTS

Residual Protective Action

After a cultivation period of 2 weeks, rice plants are sprayed with a spray mixture (0.002% active ingredient) prepared from a wettable powder formulation of the test compound. After 48 hours the treated plants are infected with a conidia suspension of the fungus. Evaluation of fungus attack is made after incubation for 5 days at 95–100% relative humidity and 24° C.

In comparison with untreated control plants (100% attack), fungus attack is less than 20% (in some cases there is no fungus attack) on rice plants which have been treated with a spray mixture containing as active ingredient one of the compounds of formula I.

We claim:

1. A pyridinyl carbonyl compound of formula I 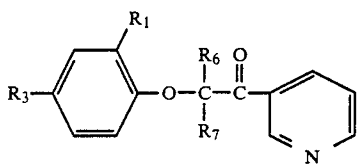 (I)

wherein $R_1$ and $R_3$ are each independently hydrogen, halogen, $C_1$–$C_4$alkyl or trifluoromethyl;

$R_6$ and $R_7$ are each independently hydrogen or $C_1$–$C_4$alkyl.

2. A compound of formula I according to claim 1 wherein $R_1$ and $R_3$ are each independently hydrogen, chlorine, methyl or trifluoromethyl;

$R_6$ is hydrogen;

$R_7$ is $C_1$–$C_4$alkyl.

3. A compound of formula I according to claim 2 wherein $R_1$ and $R_3$ are chlorine;

$R_6$ is hydrogen;

$R_7$ is $C_1$–$C_4$alkyl.

4. A compound according to claim 1 selected from the group consisting of 1-(3-pyridinyl)-2-(2,4-dichlorophenoxy)butan-1-one, 1-(3-pyridinyl)-2-(2,4-dichlorophenoxy)-isopentan-1-one, 1-(3-pyridinyl)-2-(4-chlorophenoxy)hexan-1-one, 1-(3-pyridinyl)-2-(2,4-dichlorophenoxy)-pentan-1-one, and 1-(3-pyridinyl)-2-(2,4-dichlorophenoxy)-hexan-1-one.

5. A composition for controlling microorganisms or for preventing attack by said microorganisms, which composition consists essentially of an effective amount of a compound of formula I according to claim 1, together with a suitable carrier.

6. A method of controlling phytopathogenic microorganisms or of protecting cultivated plants from attack by said microorganisms, which method comprises applying to said plants or to the locus thereof or to parts of plants a compound of formula I according to claim 1.

7. A method according to claim 6, wherein the parts of plants are seeds.

* * * * *